US012646593B2

(12) United States Patent
Suzuki et al.

(10) Patent No.: US 12,646,593 B2
(45) Date of Patent: Jun. 2, 2026

(54) MATERIAL IDENTIFICATION ASSISTANCE DEVICE, METHOD, AND PROGRAM

(71) Applicant: Hitachi, Ltd., Tokyo (JP)

(72) Inventors: Hiroyuki Suzuki, Tokyo (JP); Sayaka Kurata, Tokyo (JP)

(73) Assignee: HITACHI, LTD., Tokyo (JP)

( * ) Notice: Subject to any disclaimer, the term of this patent is extended or adjusted under 35 U.S.C. 154(b) by 442 days.

(21) Appl. No.: 18/268,395

(22) PCT Filed: Feb. 26, 2021

(86) PCT No.: PCT/JP2021/007315
§ 371 (c)(1),
(2) Date: Jun. 20, 2023

(87) PCT Pub. No.: WO2022/180776
PCT Pub. Date: Sep. 1, 2022

(65) Prior Publication Data
US 2024/0079097 A1 Mar. 7, 2024

(51) Int. Cl.
*G16C 20/20* (2019.01)
*G01N 21/31* (2006.01)
(52) U.S. Cl.
CPC ............. *G16C 20/20* (2019.02); *G01N 21/31* (2013.01)
(58) Field of Classification Search
CPC ...... G16C 20/20; G01N 21/31; G01N 23/207; G06F 18/217; G06F 18/24133;
(Continued)

(56) References Cited

U.S. PATENT DOCUMENTS

| | | | |
|---|---|---|---|
| 5,311,445 A | 5/1994 | White | |
| 10,241,040 B2 * | 3/2019 | Lambert | .............. G01N 21/359 |

(Continued)

FOREIGN PATENT DOCUMENTS

| | | |
|---|---|---|
| CN | 108827889 A | 11/2018 |
| CN | 111957600 A | 11/2020 |

(Continued)

OTHER PUBLICATIONS

International Search Report of PCT/JP2021/007315 dated Apr. 27, 2021.

(Continued)

*Primary Examiner* — Manuel A Rivera Vargas
(74) *Attorney, Agent, or Firm* — MATTINGLY & MALUR, PC

(57) ABSTRACT

A spectral analysis unit receives items of spectral data acquired by a measurement device with regards to a material according to a prescribed measurement condition, and calculates spectral feature amounts of the spectral data using a model function. A standard deviation acquisition unit estimates, on the basis of the spectral feature amounts, the standard deviation between the model function and the values actually measured by the measurement device; and a feature amount error-identification accuracy degree relationship analysis unit calculates, for each of the spectral feature amounts, an identification accuracy degree in relation to identifying the material, using spectral feature amount-material identifier correlation information indicating the correspondence relationship for the material identifier in question, and generates, using the identification accuracy degree and the standard deviation, feature amount error-identification accuracy degree correlation information indicating the correlation relationship between the identification (Continued)

accuracy degree and the spectral feature amount error for the material.

12 Claims, 12 Drawing Sheets

(58) Field of Classification Search
  CPC .......... G06N 3/084; G06N 5/01; G06N 20/20; G01J 3/0264; G01J 2003/2833; G01J 2003/2836
  See application file for complete search history.

(56) References Cited

U.S. PATENT DOCUMENTS

| | | | |
|---|---|---|---|
| 10,746,658 B1 | 8/2020 | Li et al. | |
| 2005/0002029 A1* | 1/2005 | Gornushkin | G01N 21/31 356/328 |
| 2006/0262304 A1* | 11/2006 | Carron | G01J 3/02 356/328 |
| 2007/0183568 A1 | 8/2007 | Kang et al. | |
| 2010/0100336 A1 | 4/2010 | Wright | |
| 2014/0168421 A1* | 6/2014 | Xu | G01J 3/36 348/135 |
| 2014/0185864 A1* | 7/2014 | Halper | G06V 20/13 382/103 |
| 2018/0195981 A1* | 7/2018 | Paulus | G01N 23/087 |
| 2019/0234866 A1* | 8/2019 | Hsiung | G01N 21/255 |
| 2020/0284719 A1 | 9/2020 | Iqbal et al. | |

FOREIGN PATENT DOCUMENTS

| | | |
|---|---|---|
| CN | 112162041 A | 1/2021 |
| EP | 3339840 A1 | 6/2018 |
| EP | 3477282 A1 | 5/2019 |
| JP | 2006-084350 A | 3/2006 |
| JP | 2007-183277 A | 7/2007 |
| JP | 2013-064726 A | 4/2013 |
| JP | 2015-158439 A | 9/2015 |
| JP | 2018-100903 A | 6/2018 |
| JP | 2019-082459 A | 5/2019 |
| JP | 2019-148583 A | 9/2019 |

OTHER PUBLICATIONS

Extended European Search Report received in corresponding European Application No. 21927878.5 dated Oct. 25, 2024.

Oviedo, F. et al., "Fast classification of small X-ray diffraction datasets using physics-based data augmentation and deep neural networks", 32nd Conference on Neural Processing Systems, Nov. 20, 2018, pp. 1-11.

* cited by examiner

FIG. 2

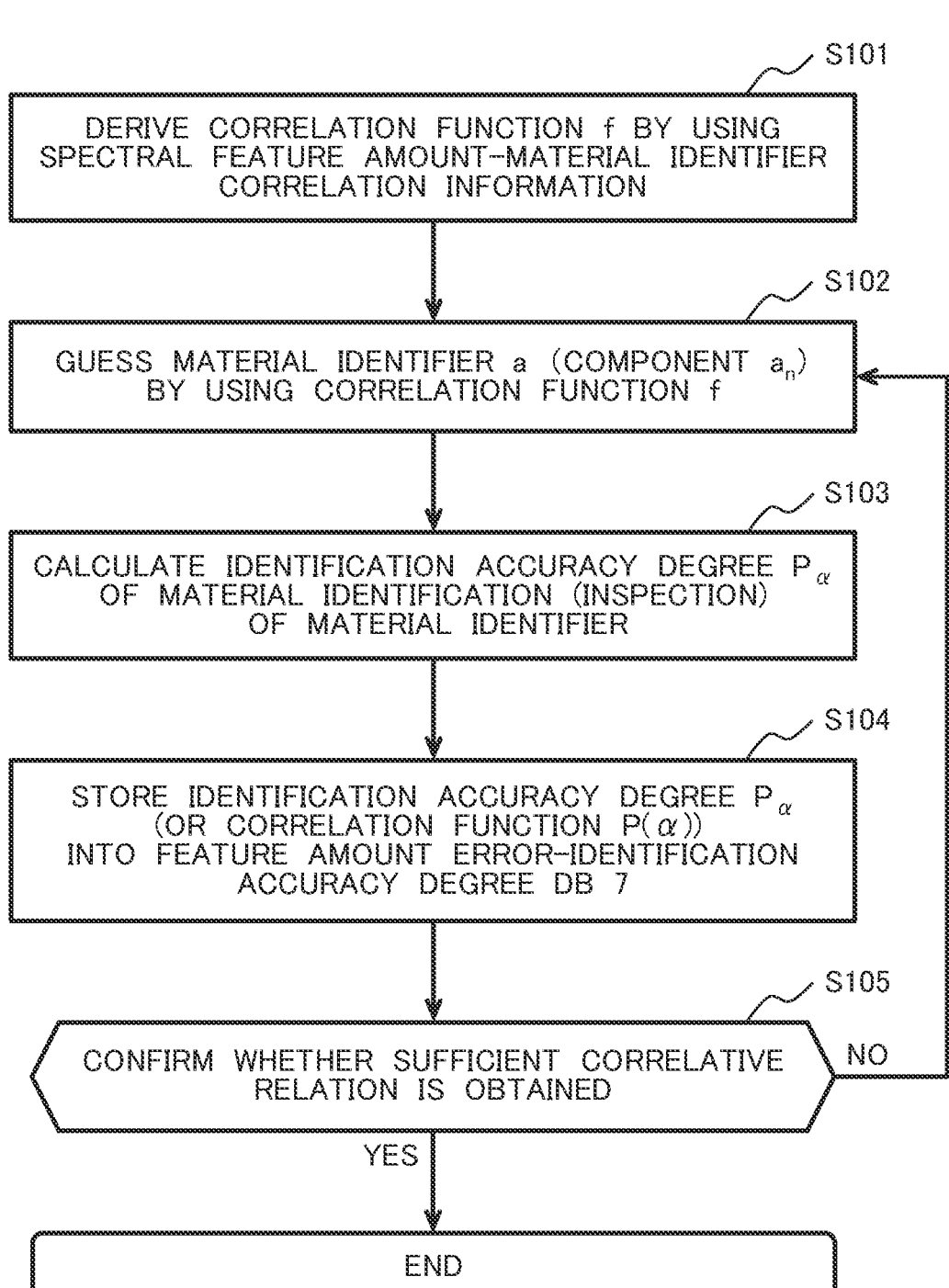

S101

DERIVE CORRELATION FUNCTION f BY USING
SPECTRAL FEATURE AMOUNT-MATERIAL IDENTIFIER
CORRELATION INFORMATION

S102

GUESS MATERIAL IDENTIFIER a (COMPONENT $a_n$)
BY USING CORRELATION FUNCTION f

S103

CALCULATE IDENTIFICATION ACCURACY DEGREE $P_\alpha$
OF MATERIAL IDENTIFICATION (INSPECTION)
OF MATERIAL IDENTIFIER

S104

STORE IDENTIFICATION ACCURACY DEGREE $P_\alpha$
(OR CORRELATION FUNCTION $P(\alpha)$)
INTO FEATURE AMOUNT ERROR-IDENTIFICATION
ACCURACY DEGREE DB 7

S105

CONFIRM WHETHER SUFFICIENT CORRELATIVE
RELATION IS OBTAINED

NO

YES

END

*FIG. 6*

| TECHNIQUES USED | RANDOM FOREST (RF) METHOD | NEURAL NETWORK (NN) METHOD |
|---|---|---|
| MATERIAL IDENTIFICATION ACCURACY DEGREE | 94.7% | 94.8% |

|  A |  a+, a- |
|---|---|

Correct class: 0 , Predicted class: 0 0
Correct class: 1 , Predicted class: 1 1
Correct class: 2 , Predicted class: 12 2
Correct class: 3 , Predicted class: 3 3
Correct class: 4 , Predicted class: 4 4
Correct class: 5 , Predicted class: 5 5
Correct class: 6 , Predicted class: 6 6
Correct class: 7 , Predicted class: 7 7
Correct class: 8 , Predicted class: 8 8
Correct class: 9 , Predicted class: 9 2
Correct class: 10 , Predicted class: 10 10
Correct class: 11 , Predicted class: 11 11
Correct class: 12 , Predicted class: 12 12
Correct class: 13 , Predicted class: 13 13
Acurracy: 92.85714285714286

α = [-0.626278, 0.30263084, 0.10266177, 0.50424665, -0.3697153, -0.51667094, -0.7294119, -0.35774174, -0.52728623, 0.5542312, -0.3964884, 0.04036945, -0.5232295, -0.91357, -0.5400572, 0.7587115, 0.5876496, 0.35601735, -0.67772794, 0.09602686, -0.7297397, -0.8667195, -0.30359778, 0.25141755, -0.50660187, 0.8223287, -0.3945051, 0.65390307]

|  A |  a+, a- |
|---|---|

Correct class: 0 , Predicted class: 0 0
Correct class: 1 , Predicted class: 1 1
Correct class: 2 , Predicted class: 2 6

⋮

FIG. 8
(a)
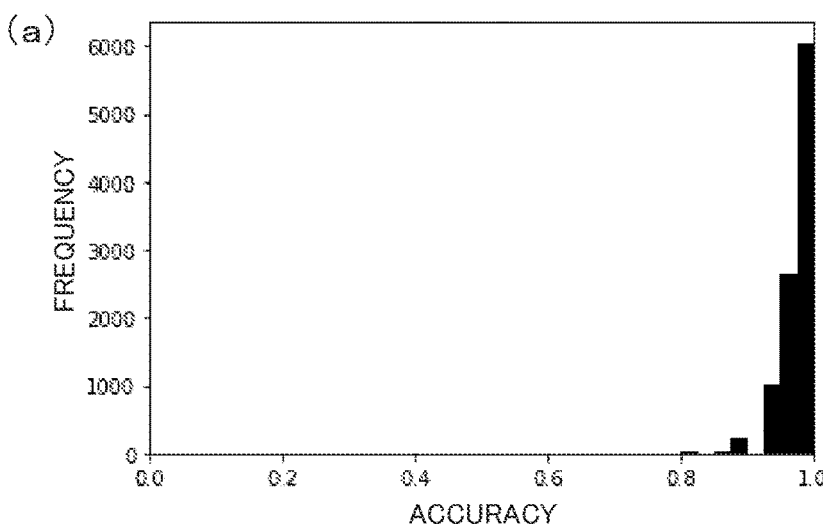
(b)
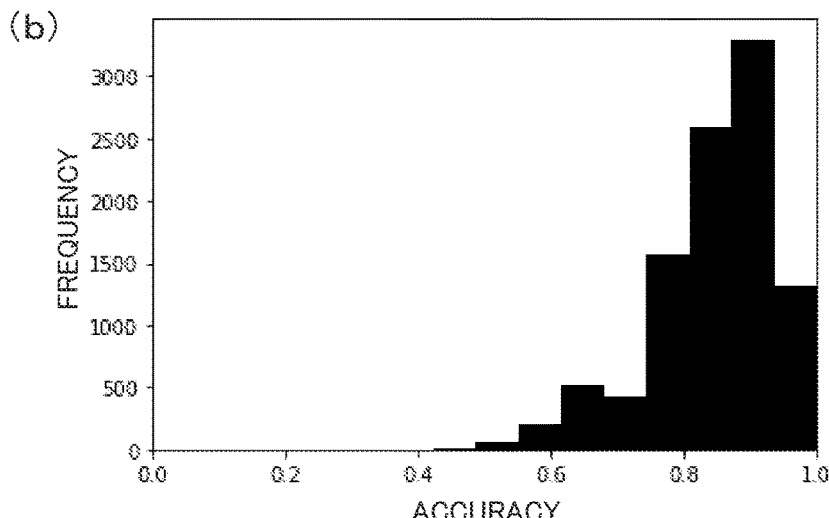
(c)
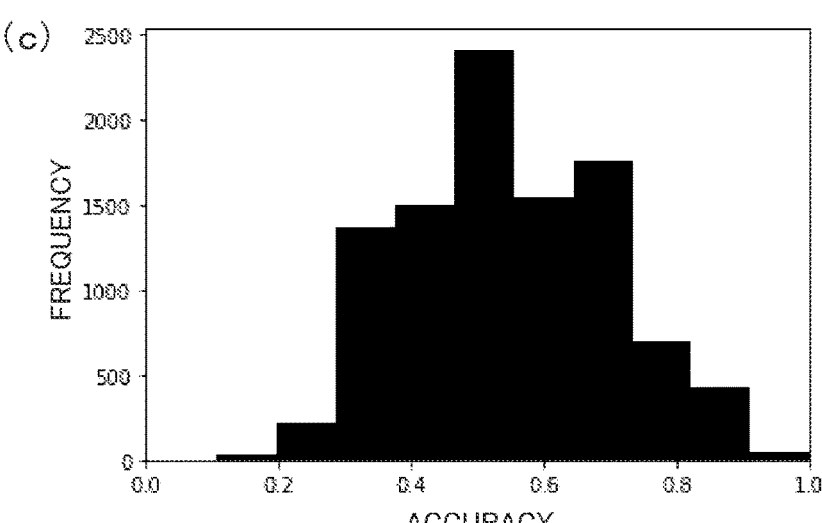

*FIG. 9*

| | INHIBITER I | | | | INHIBITER II | | | | (110) | | | | ... | (310) | | | |
|---|---|---|---|---|---|---|---|---|---|---|---|---|---|---|---|---|---|
| | $H_k$ err | $X_o$ err | Int_err | $\eta$_err | $H_k$ err | $X_o$ err | Int_err | $\eta$_err | $H_k$ err | $X_o$ err | Int_err | $\eta$_err | ... | $H_k$ err | $X_o$ err | Int_err | $\eta$_err |
| I | 5.82 E-3 | 1.52 E-3 | 232 | 9.70 E-2 | 3.39 E-2 | 2.58 E-4 | 331 | 4.11 E-1 | 8.22 E-4 | 2.37 E-4 | 138 | 4.32 E-2 | ... | 2.68 E-3 | 8.11 E-4 | 281 | 5.33 E-2 |
| II | 0 | 0 | 0 | 0 | 0 | 0 | 0 | 0 | 3.10 E-4 | 8.89 E-5 | 219 | 1.88 E-2 | ... | 1.29 E-4 | 3.58 E-4 | 212 | 3.86 E-2 |

FIG. 10

|  | P($\sigma$) |
|---|---|
| SPECTRAL DATA I | 96.2 % |
| SPECTRAL DATA II | 96.2 % |

|  | MOST FREQUENT VALUE OF P($\sigma$) | ACCURACY DEGREE IN f(m) |
|---|---|---|
| 413 PIECES OF SPECTRAL DATA FOR VERIFICATION | 96.2 % | 80.7 % |

(b)

| SPECTRAL DATA No. | CALCULATION ACCURACY DEGREE FROM P($\sigma$) | CLASS WHICH IS PREDICATED FROM f(m) | ACCURATE CLASS |
|---|---|---|---|
| 1 | −7.5 % | 12 | 12 |
| 2 | −725491 % | 12 | 13 |
| 3 | −74556 % | 9 | 9 |
| 4 | −99.9 % | 9 | 9 |
| 5 | −515337 % | 7 | 2 |
| 6 | −757648 % | 12 | 8 |
| 7 | −1015650 % | 1 | 1 |
| 8 | −59.4 % | 7 | 3 |
| 9 | −1.4 % | 3 | 3 |
| 10 | 37.3 % | 12 | 5 |
| 11 | −84.3 % | 6 | 6 |
| 12 | −837072 % | 7 | 6 |

ACCURACY DEGREE : 50 % (6/12)

MATERIAL IDENTIFICATION ASSISTANCE DEVICE, METHOD, AND PROGRAM

TECHNICAL FIELD

The present invention relates to a technology for assisting identification of a material. Incidentally, the material includes a source material, a raw material, an ingredient, a component and a constituent thereof, a sample and so forth. In addition, inspection thereof is included in the identification of the material.

BACKGROUND ART

At present, an identification technology for specifying the material is requested. For example, in the midst of diversifying supply chains, the problem of the so-called silent change is getting more serious. The silent change means that the specification thereof is changed without informing a company which is an ordering source of the material of it. In order to suppress this silent change, it is important to secure the reliability of the material in the supply chain and an inspection technology of collating analysis data which is low in acquisition cost with a precomposed material database (DB) and specifying the material is necessary.

In Patent Document 1, a method of databasing spectrums of a plurality of materials, calculating a locally changed value which was normalized between a target sample and the spectrum of each reference sample in the database as a feature amount, finding a degree of similarity and thereby identifying the sample is disclosed in Patent Document 1.

CITATION LIST

Patent Literature

PTL 1: Publication of US Patent Application No. 2020/0284719

SUMMARY OF INVENTION

Technical Problem

Here, in the material identification, it is generally performed to extract the feature amount by approximating data (in the following, spectral data) that output is described as a single-valued function of input by a model function. The method of identifying the material by inquiring the material DB which stores a correspondence relation between the feature amount of the material and an identifier about the feature amount which was extracted from the spectrum of a sample to be expected and which is described in the Patent literature 1 is effective for the spectral data which was measured with high accuracy.

However, in the Patent Literature 1, there is a tendency toward becoming excessive in accuracy in an inspection that a low data acquisition cost is desired and there is an issue. In addition, in a case where different business operators perform the operation of the material DB and the acquisition of the inspection data, it is desired to acquire sufficiently accurate data with no inquiry to the highly confidential material DB about the feature amount.

Accordingly, an object of the present invention is to make material identification which includes the material inspection possible regardless of the accuracy of the material DB and presence/absence thereof.

Solution to Problem

In order to attain the above object, in the present invention, it aims to analyze relationship between a feature amount error and an identification accuracy degree in the material identification and to make a result thereof utilizable in the material identification.

One aspect of the present invention which is more concrete is, in a material identification assistance device which assists material identification, the material identification assistance device which has a spectral analysis unit which accepts a plurality of pieces of spectral data which was acquired by a measurement device in accordance with a predetermined measurement condition to the material and calculates a spectral feature amount of the spectral data by using a model function, a standard deviation acquisition unit which estimates a standard deviation between the model function and a value which is actually measured by the measurement device on the basis of the spectral feature amount and a feature amount error-identification accuracy degree relationship analysis unit which calculates an identification accuracy degree when identifying the material by using spectral feature amount-material identifier correlation information which indicates a correspondence relation between material identifiers concerned per spectral feature amount and generates feature amount error-identification accuracy degree correlation information which indicates a correlative relation between a spectral feature amount error and the identification accuracy degree of the material by using the identification accuracy degree concerned and the standard deviation and makes identification to the material possible on the basis of the feature amount error-identification accuracy degree correlation information.

In addition, a material identification assisting method which used the material identification assistance device and a material identification assisting system which includes this are also included in the present invention. Further, also a program for making the material identification assistance device function as a computer and a storage medium which stores this are also included in the present invention. And, still further, also a material identification technology which utilizes the material identification assistance device is one aspect of the present invention.

Advantageous Effects of Invention

According to the present invention, material identification which includes the material inspection becomes possible regardless of the accuracy of the material DB and presence/absence thereof.

BRIEF DESCRIPTION OF DRAWINGS

FIG. 2 is a flowchart showing processing of a feature amount error-identification accuracy degree relationship analysis unit pertaining to the embodiment 1.

FIG. 6 is a table showing a relationship between a spectral feature amount and a material identifier in a case example 1.

FIG. 7 is a display example of a feature amount error and identification accuracy degree relationship analysis unit in the case example 1.

FIG. 8 is diagrams showing frequency distributions of material identification accuracy degrees which are output when adding/subtracting the feature amount error to/from the feature amount and inputting them into a correlation function f in the case example 1.

FIG. 9 is a table showing some of components of a standard deviation σ in a case example 2.

FIG. 10 is a table showing an output result when inputting the standard deviation σ in the case example 2 into $P_\alpha$ or $P(\alpha)$.

FIG. 11 is tables of mutually comparing the accuracy degrees of the material identification in a case where a spectrum feature amount m was used, and in a case where a standard deviation σ was used in the case example 2.

DESCRIPTION OF EMBODIMENTS

In the following, each embodiment of the present invention will be described by using the drawings. Incidentally, in each embodiment, a case where material identification is performed and then inspection is performed will be described by way of example. That is, in each embodiment, as one example of a material identification system and a material identification device, a material inspection assistance system 1000 and a material inspection assistance device 100 will be used.

Embodiment 1

Figure 1:
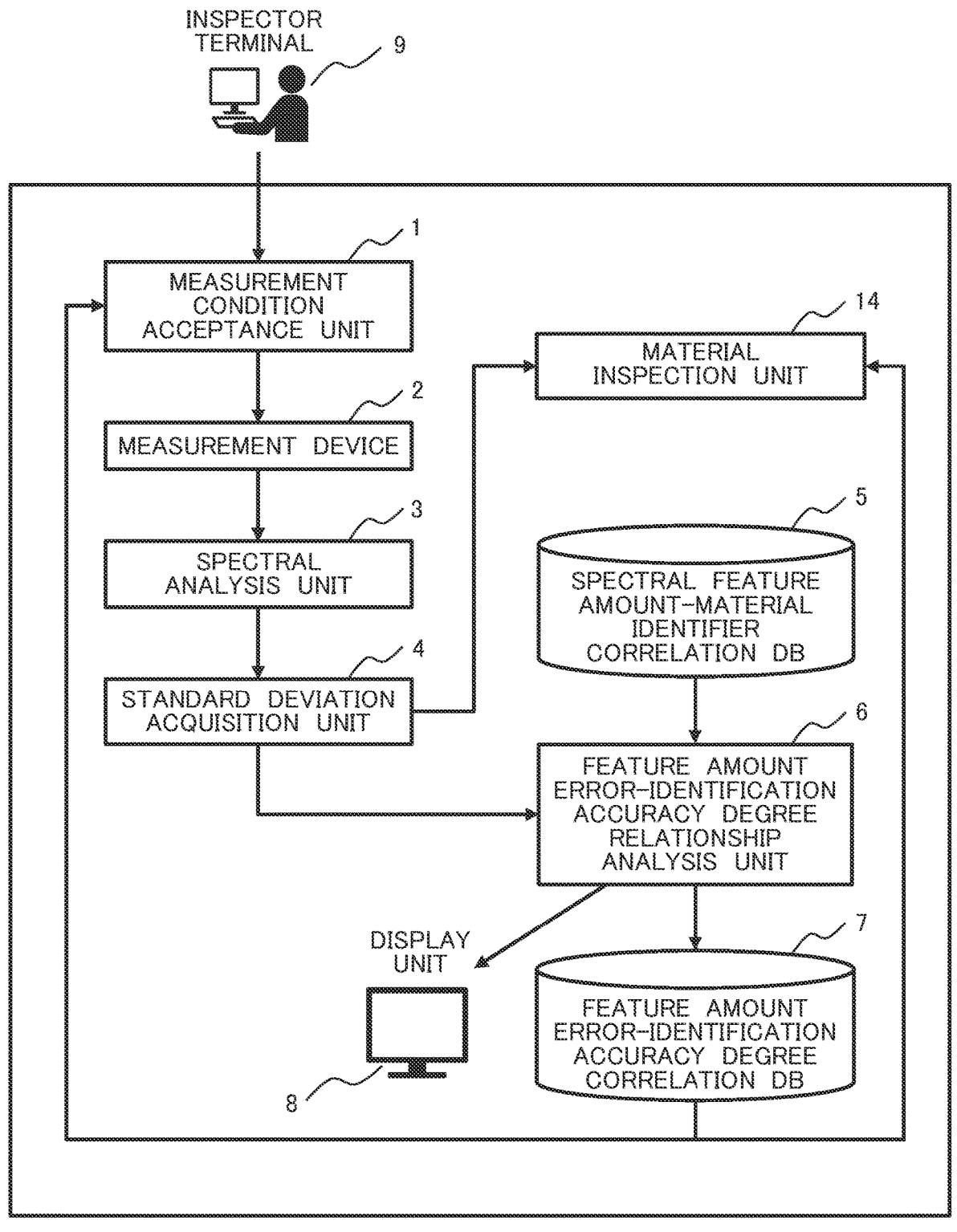
FIG. 1 is a diagram explaining processing details and a function block of a material inspection assistance system pertaining to an embodiment 1.

First, the embodiment 1 will be described. FIG. 1 is a diagram explaining processing details and a functional block of the material inspection assistance system 1000 pertaining to the present embodiment. The material inspection assistance system 1000 is adapted to assist decision of an effective inspection condition. Incidentally, in the present embodiment, although it targets at the inspection assistance and therefore the inspection condition is used, it is also possible to widely seek for an identification condition for identification. Accordingly, as shown in FIG. 1, it is equipped with a measurement condition acceptance unit 1, a measurement device 2, a spectral analysis unit 3, a standard deviation acquisition unit 4, a spectral feature amount-material identifier correlation DB 5 which is a material DB, a feature amount error-identification accuracy degree relationship analysis unit 6, a feature amount error-identification accuracy degree correlation DB 7, a display unit 8, an inspector terminal 9 and a material inspection unit 14. Although this material inspection assistance system 1000 can be realized by a so-called computer system, details thereof will be described later.

First, the measurement condition acceptance unit 1 accepts a measurement condition of measurement for inspection by the inspector terminal 9. Incidentally, the accuracy of spectral data which is obtained varies depending on the measurement condition which is accepted. In addition, the measurement condition indicates a device-derived parameter which affects the accuracy of the spectral data and that a user (the inspector) of the inspector terminal 9 can change.

In addition, the measurement device 2 is the device which outputs the spectral data. The measurement device 2 to be utilized is selected on the basis of an analytical method by which a spectral feature amount which is suited to an inspection item to the material can be evaluated. In addition, the spectral analysis unit 3 is adapted to accept the spectral data from the measurement device 2, to approximate the spectrum by a model function and to calculate the spectral feature amount which is the feature amount thereof. Here, the model function is, the one which can approximate the spectral shape of the spectrum is selected and approximation is executed by the spectral analysis unit 3 by the least-square method.

The standard deviation acquisition unit 4 is adapted to estimate (acquire) a standard deviation which is a squared mean error between an actually measured value and a model function from model function approximation of the spectrum. The spectral feature amount-material identifier correlation DB 5 is, spectral feature amount-material identifier correlation information which indicates a correlative relation between the feature amount which is extracted from the spectrum and an identifier which discriminates the material stores.

The feature amount error-identification accuracy degree relationship analysis unit 6 is adapted to calculate the identification accuracy degree of the material when introducing the error into the spectral feature amount. In addition, the feature amount error-identification accuracy degree relationship analysis unit 6 generates feature amount error-identification accuracy degree correlation information which indicates the correlative relation between this identification accuracy degree and the spectral feature amount error. Therefore, the feature amount error-identification accuracy degree relationship analysis unit 6 evaluates robustness of the spectral feature amount-material identifier correlation DB 5 to the feature amount error.

In addition, the feature amount error-identification accuracy degree correlation information which is a result which was obtained by the feature amount error-identification accuracy degree relationship analysis unit 6 is stored into the feature amount error-identification accuracy degree correlation DB.

In addition, the display unit 8 displays a result of processing and so forth in each unit such as the accuracy degree of the material identification which is calculated from the feature amount error and so forth. In addition, the display unit 8 may be realized by a display screen which is installed on the device and may be also realized by an individual terminal device. Further, the inspector terminal 9 is a terminal device that the inspector utilizes.

Still further, the material inspection unit 14 specifies the measurement condition of the measurement device 2 at the time of inspection by using the feature amount error-identification accuracy degree correlation information and executes the inspection on the basis of this. Incidentally, the material inspection unit 14 is adapted to perform inspection as one example of material identification and may be also realized as a material identification unit.

In the above configuration, the material inspection assistance system 1000 executes the following processing. First, the measurement condition acceptance unit 1 accepts the measurement condition from the inspector terminal 9. Next, the measurement device 2 performs measurement on the material in accordance with a predetermined measurement condition and acquires a plurality of pieces of spectral data.

Next, the spectral analysis unit 3 calculates the spectral feature amount of the spectral data which was obtained by the measurement device 2 by using a model function. Next, the standard deviation acquisition unit 4 estimates the standard deviation between the model function and the actually measured value by the measurement device 2 on the basis of the spectral feature amount.

Next, the feature amount error-identification accuracy degree relationship analysis unit 6 calculates the identification accuracy degree when inspecting the material by using the spectral feature amount-material identifier correlation information which indicates a correspondence relation between it and the material identifier concerned per spectral feature amount. Then, the feature amount error-identification accuracy degree relationship analysis unit 6 generates the feature amount error-identification accuracy degree correlation information which indicates the correlative relation between the spectral feature amount error and the identification accuracy degree of the material to be inspected by using the identification accuracy degree concerned and the standard deviation. In addition, the display unit 8 displays the generated feature amount error-identification accuracy degree correlation information. Further, the feature amount error-identification accuracy degree relationship analysis unit 6 stores the generated feature amount error-identification accuracy degree correlation information into the feature amount error-identification accuracy degree correlation DB 7.

Then, the material inspection unit 14 specifies the measurement condition under which the inspection is performed by using the spectral feature amount of the inspection object and the feature amount error-identification accuracy degree correlation information and performs inspection on the material.

Next, the processing of the feature amount error-identification accuracy degree relationship analysis unit 6 will be described by using a flowchart which is shown in FIG. 2.

First, in step S101, the feature amount error-identification accuracy degree relationship analysis unit 6 derives a correlation function f by using the spectral feature amount-material identifier correlation information in the spectral feature amount-material identifier correlation DB 5. This correlation function f takes a parameter value m (a component is mi in vector quantity), i is the total number of parameters which were obtained by model function approximation, in the following, simply denoted as "a parameter value m") which indicates the spectral feature amount of a model function which approximated the spectrum as input and takes a material identifier A (the component is $A_n$ in vector quantity, n is the number of the kinds of the materials) as output.

Next, in step S102, the feature amount error-identification accuracy degree relationship analysis unit 6 calculates a material identifier $a_\pm$ (the component is $a_{2n}$ in vector quantity) by using the correlation function f. Here, in the correlation function f, a relation of A=f(m) is established. Thus, in the present step, it calculates the material identifier $a_\pm$ (the component $a_{2n}$) by inputting m±α (α is the vector quantity and a component $\alpha_1$ is a positive real number) into that correlation function f.

That is, next, in step S103, the feature amount error-identification accuracy degree relationship analysis unit 6 calculates an identification accuracy degree $P_\alpha$ in the inspection of the material per material identifier. Here, it is presupposed that a relation of $a_\pm$=f(m±α) (double-sign correspondence) would be established. Then, the feature amount error-identification accuracy degree relationship analysis unit 6 calculates a material identifier a which is estimated from spectral feature amount-material identifier correlation information when an error has been introduced into the spectral feature amount. Here, to mutually add/subtract two free vectors m and a corresponds to equivalent deformation of spatial base vectors and it is important that the size of a space which is spanned with the base vector and the size of a space of its mapping destination are not changed. This is because, if only one of $a_\pm$ is calculated and used, it will become impossible to estimate the accuracy degree of material identification from the measurement condition with sufficient accuracy.

Therefore, the feature amount error-identification accuracy degree relationship analysis unit 6 compares an estimated value a of the material identifier which was obtained in this way with the correct value A and calculates a concordance rate of each component as the identification accuracy degree $P_\alpha$ of the material identification.

Here, it becomes possible to accept the standard deviation which is calculated from the measurement condition in a state that a sufficient estimation accuracy is maintained by setting to Pc, that a vector space of the accuracy degree $P_{\pm\alpha}$ of the material identification has been halved. Then, in step S104, the feature amount error-identification accuracy degree relationship analysis unit 6 stores the identification accuracy degree Pc, (or the correlation function P(α) into the feature amount error-identification accuracy degree DB 7. Thereby, the feature amount error-identification accuracy degree relationship analysis unit 6 generates the feature amount error-identification accuracy degree correlation information which indicates the correlative relation between the spectral feature amount error and the identification accuracy degree Pc, and stores this into the feature amount error-identification accuracy degree DB 7.

Next, in step S105, step S102 to step S104 are repeated until the identification accuracy degree Pc, of the number (the number of times which has been set in advance) which is sufficient to guess the accuracy degree of the material identification from the measurement condition in accordance with the control of the feature amount error-identification accuracy degree relationship analysis unit 6. In the present embodiment, it is desirable to give each component of α in magnitude which is less than the degree which is the same as that of an error which would occur. Incidentally, as a condition for repeating them, it is not limited to the sufficient number. It is good enough to meet a predetermined standard which has been determined in advance.

In addition, it becomes possible to qualify the robustness of the spectral feature amount-material identifier correlation DB 5 against the feature amount error by using this processing flow which is shown in FIG. 2 and cross-DB abilities can be evaluated without relying on cross-validation. That is expressed by $P_{\alpha D}/P_o$ and normalizes an accuracy degree $P_{oD}$ of the material identification when inputting the standard deviation $\sigma_D$ of the feature amount data group which was used when preparing the spectral feature amount and material identifier correlation DB 5 with an accuracy degree $P_o$ of the material identification when α=0.

Next, processing for the inspection using the feature amount error-identification accuracy degree correlation information will be described by using FIG. 3. Here, the processing for the inspection includes determination of the inspection condition and the inspection itself.

When an inspector arranges at least one sample in a group of target materials on the measurement device 2, the measurement device 2 detects this in step S201. There is no problem when this sample is the same as the spectral feature amount and material identifier correlation DB 5 in system and also it may be a sample which is not recorded in the spectral feature amount-material identifier correlation information.

Next, in step S202, the measurement condition acceptance unit 1 accepts the measurement condition which has been input into the inspector terminal 9. Then, the measurement device 2 measures the sample in accordance with this measurement condition and acquires the spectrum.

Next, the spectral analysis unit 3 approximates the spectrum by a model function and calculates the spectral feature amount and the standard deviation thereof. For this purpose, the spectral analysis unit 3 approximates the spectrum by a model function M and calculates the parameter value m and the standard deviation σ thereof.

Next, in step S204, the standard deviation acquisition unit 4 acquires the standard deviation. Then, the material inspection unit 14 specifies the material identification accurate degree by using this standard deviation and the feature amount error-identification accuracy degree correlation DB 7. For this purpose, the material inspection unit 14 specifies the material identification accuracy degree which is estimated from the spectral feature amount-material identifier correlation DB 5 when it was measured under the above-mentioned measurement condition by collating the standard deviation with the feature amount error-identification accuracy degree correlation DB 7.

Next, in step S205, the inspector terminal 9 displays a result thereof. Therefore, the inspector can decide whether the data accuracy is sufficient to meet required specifications by confirming the material identification accurate degree which was estimated from the measurement condition. Then, the inspector terminal 9 accept in a case where the sufficient material identification accuracy degree can be obtained, it shifts to step S206. In a case where it cannot be obtained, it returns to step S202.*s* a judgement result from the inspector. As a result, Then, the material inspection unit 14 executes sample inspection by using the feature amount error-identification accuracy degree correlation information on the material identification accuracy degree which has been decided to be sufficient in accordance with the measurement condition in step S202, that is, the inspection condition. Description of the embodiment 1 ends with the above.

Embodiment 2

Figure 4:
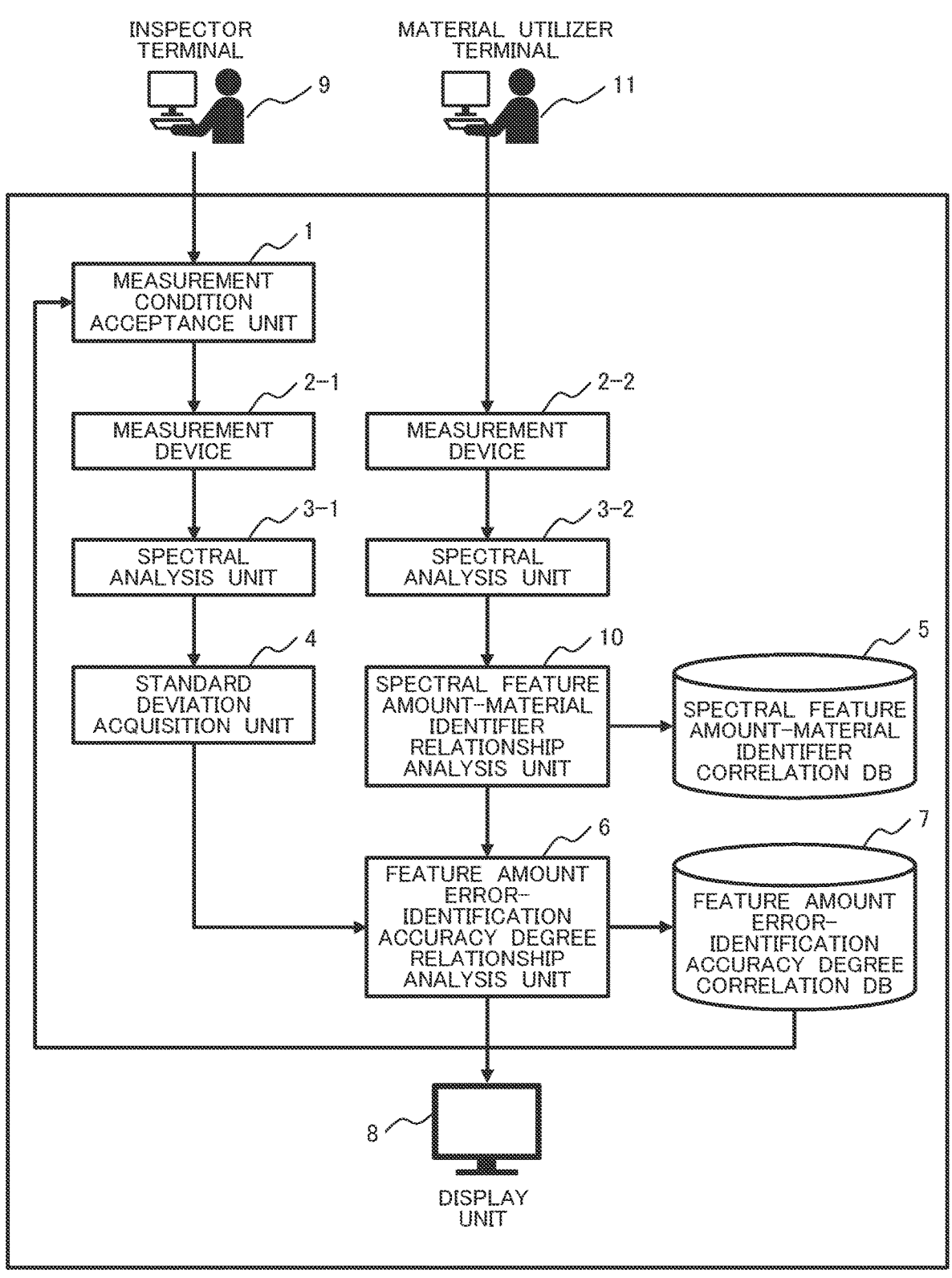
FIG. 4 is a diagram explaining processing details and a function block of a material inspection assistance system pertaining to an embodiment 2.

Next, the embodiment 2 is the embodiment of generating the spectral feature amount-material identifier correlation information in the spectral feature amount-material identifier correlation DB 5. FIG. 4 is the diagram for explaining the processing details and the function block of the material inspection assistance system 1000 pertaining to the present embodiment. The material inspection assistance system 1000 in the second embodiment 2 is adapted to assist effective determination of the inspection condition. In addition, as shown in FIG. 4 as the constitutional parts which are the same as those in FIG. 1, it is equipped with the measurement condition acceptance unit 1, a measurement device 2-1, a spectral analysis unit 3-1, the standard deviation acquisition unit 4, the spectral feature amount and material identifier correlation DB 5, the feature amount error-identification accuracy degree relationship analysis unit 6 and the feature amount error and identification accuracy degree correlation DB 7. Here, the measurement device

2-1 and the spectral analysis unit 3-1 are the ones which correspond to the measurement device 2 and the spectral analysis unit 3 in FIG. 1.

In addition, in the present embodiment, also a material utilization/application business operator who purchases the material to be inspected and manufactures products pertains thereto, other than the inspection business operator of the inspector. It is different from the embodiment 1 in the point that a measurement device 2-2, a spectral feature amount-material identifier relationship analysis unit 10 and a spectral analysis unit 3-2 are newly added in association with this. Although the measurement device 2-2 may be different from the measurement device 2-1, they are the same as each other in the analysis method and the correspondence relation is necessary at least in an inter-device parameter. The spectral analysis unit 3-2 is adapted to extract the spectral feature amount by approximating the spectrum by the model function which is the same as that of the spectral analysis unit 3-1. Accordingly, the measurement device 2-2 and the spectral analysis unit 3-2 may be shared with the measurement device 2-1 and the spectral analysis unit 3-1.

Here, the spectral feature amount-material identifier relationship analysis unit 10 prepares the spectral feature amount-material identification accuracy degree information by using the spectral feature amount which is output from the spectral analysis unit 3-2 and stores it into the spectral feature amount-material identification accuracy degree correlation DB 5.

In the embodiment 2, the application thereof to such a business scene as that which is, for example, described below is supposed. A material utilization/application business operator places an order to a material manufacturer in the form of a specification which is peculiar to each business operator and therefore the confidentiality of the spectral feature amount-material identifier correlation DB 5 which is the material DB is high and it is often the case that the material utilization/application business operator himself constructs and operates the spectral feature amount-material identifier correlation DB 5. On the other hand, it is often the case that an external inspection business operator performs inspection of the accepted materials for a reason of the running cost.

In this case, the material utilization/application business operator makes a request to an inspection business operator for data which has a sufficient accuracy in the material inspection. On the other hand, it is necessary for the inspection business operator who handles specimens of a plurality of material utilization/application business operators to acquire inspection data which makes it possible to exhibit a sufficient material identification accuracy degree without gaining access to the spectral feature amount-material identifier correlation DB 5 at the lowest possible cost. Accordingly, although the appropriate inspection condition is settled by performing negotiations between the both business operators a plurality of times, the economic efficiency is liable to be lost because it needs time and labor. Therefore, the material inspection assistance system 1000 of the second embodiment is suitable for such an industry.

Figure 3:
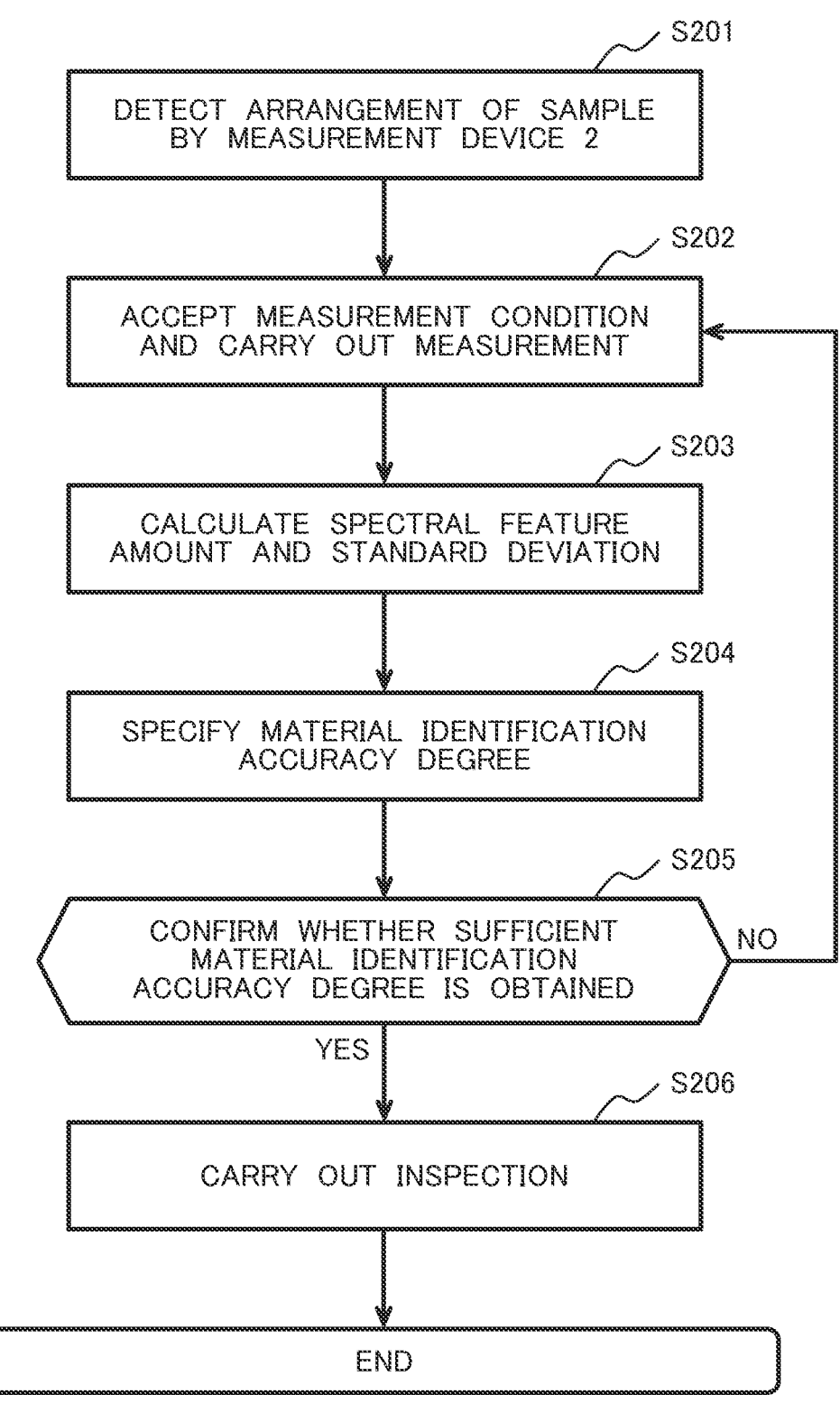
FIG. 3 is a flowchart showing processing for the inspection pertaining to the embodiment 1.

Here, a flowchart up to determination of the inspection condition which is necessary to perform material identification from the spectral feature amount in the present embodiment and a processing flow for preparing the feature amount error-identification accuracy degree correlation information are the same as those in FIG. 2 and FIG. 3 respectively. Description of the embodiment 2 is completed as above.

Embodiment 3

Figure 5:
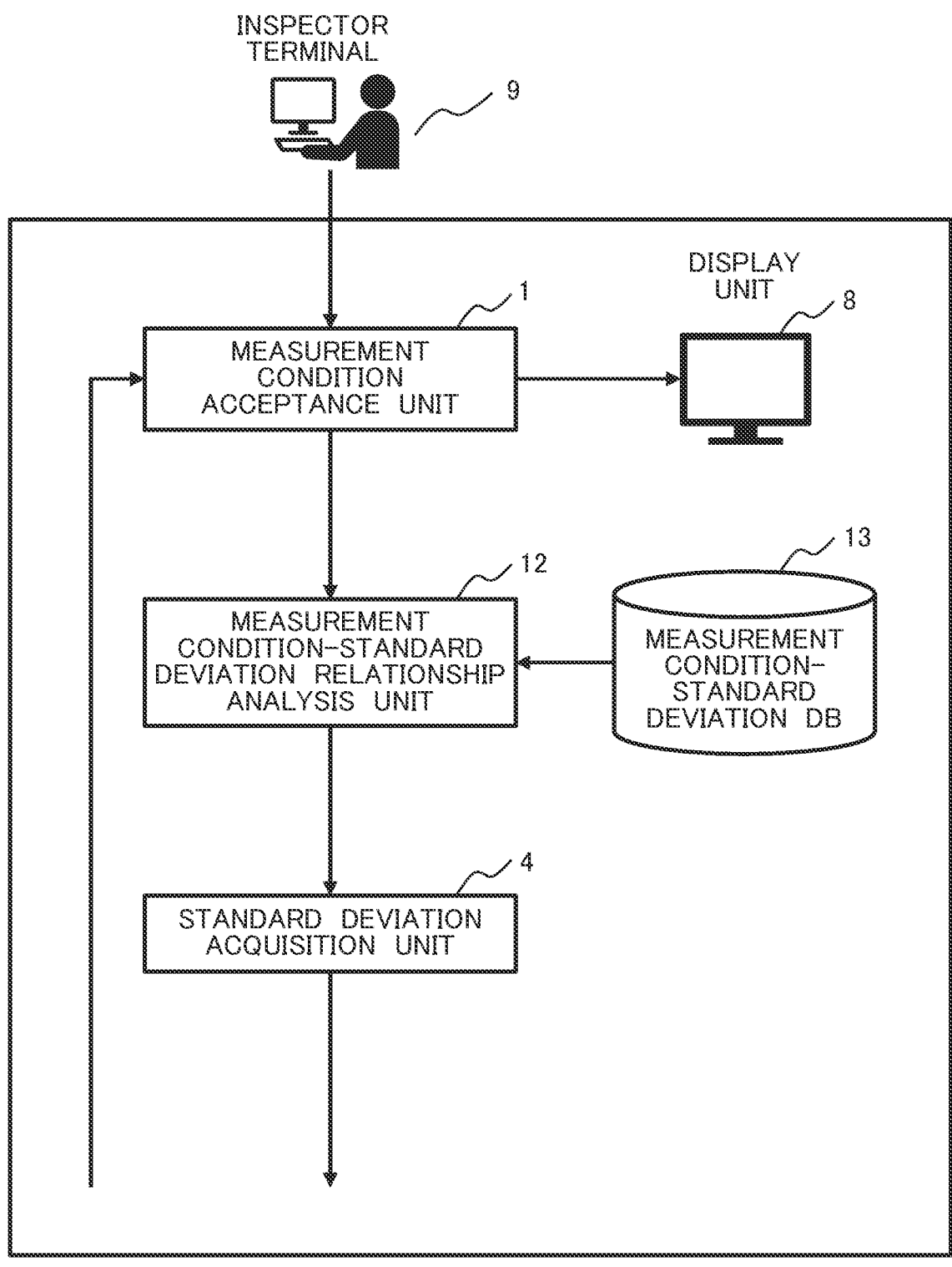
FIG. 5 is a diagram (partial) explaining processing details and a function block of a material inspection assistance system pertaining to an embodiment 3.

Next, the embodiment 3 will be described. FIG. 5 is a diagram showing processing details and a part of the function block of the material inspection assistance system 1000 pertaining to the present embodiment. In the present embodiment, it is an embodiment that the measurement device 2 and the spectral analysis unit 3 in the embodiments 1 and 2 are replaced with a measurement condition-standard deviation relationship analysis unit 12 and a measurement condition-standard deviation DB 13.

In this way, in the embodiment 3, it functions by replacing parts of the embodiments 1 and 2 with configurations which are shown in FIG. 5. The measurement condition-standard deviation relationship analysis unit 12 which is a concrete replaced configuration calculates the standard deviation by inputting the measurement condition and the material identifier. This standard deviation is obtained by approximating the spectral data by a model function. Then, a measurement condition-derived factor and a material-derived (including a model function-derived one) factor are included in this standard deviation. Although it is possible to calculate the standard deviation also by inputting only the measurement condition into this correlation function g, since it can be calculated with a high accuracy by also including the material identifier in the input, it is more desirable.

Therefore, in the present embodiment, the measurement condition-standard deviation relationship analysis unit 12 calculates the standard deviation from the measurement condition. Then, the standard deviation acquisition unit 4 calculates the accuracy degree of material identification from that standard deviation. As a result, when the measurement condition is input, the material inspection assistance system 1000 can display the accuracy degree of the material identification on the display unit 8.

That is all for description of each embodiment and, in the following, case examples in a case where processing of each embodiment has been executed will be described. Incidentally, the present invention is not limited to these embodiments and case examples.

Case Example 1

The case example 1 is a case example of performing identification of motor-use electromagnetic steel plates of electrically-powered vehicles. At present, in a situation that electrification of the vehicles is promoted, the percentage of foreign-made materials in the motor-use electromagnetic steel plates is increased. In a case where the final product of a material supply chain endangers human life as in the case of vehicle members, it is extremely important to suppress silent change. Accordingly, we verified the effects of 14 kinds of motor-use electromagnetic steel plates (non-oriented electromagnetic steel plates) in the case example 1.

Objective functions of the electromagnetic steel plate are a magnetic property and a mechanical strength and a crystal grain size distribution, a crystal orientation distribution, a stress distribution, minor components and so forth of a material composition are given as explanatory variables of those objective functions. In general, since the explanatory variable is larger than the objective function in information amount, a material structure-derived feature amount is appropriate as the feature amount for identifying the electromagnetic steel plate. In addition, from the viewpoint of inspection, an analytical method by which average or statistical information on a material composition can be obtained with ease is appropriate. Since a 2θ method of X-ray diffraction (XRD) enables to obtain the stress distribution, the crystalline orientation distribution, a crystal grain size, a lattice constant and material composition-derived feature amounts of foreign substances and so forth of the material with ease and these are the spectral data, it is appropriate as an analytical method of validating the effect of the case example 1 and thus it was selected.

In the present case example, data such as the following was used in order to construct the spectral feature amount-material identifier correlation DB 5 which is the material DB. 114 pieces of data was used in total, that the measurement device 2 obtained by irradiating two samples which were changed in clipping position further with X-ray beams in parallel with a rolling direction (RD) or a vertical direction (TD) and by scanning a range from 20° to 120° in 2θ at a speed of 10°/min. or 20°/min. In addition, rear faces of some samples were also measured.

The spectral analysis which was carried out in the present case example was executed by approximating the spectral shape by the Pseudo-Voigt function by using the least square method. When approximating it by the Pseudo-Voigt function, four feature amounts, in total, of a peak half-value width $H_k$, a diffraction position $X_o$, an integrated intensity I and a Lorenz component ratio η (a Gaussian component ratio is 1−η) are calculated.

In addition, diffraction peaks which are observed are an inhibiter I in the vicinity of 20°, an inhibiter II in the vicinity of 35° and main phase-derived five ones ((110) (200) (211) (220) and (310) which amount to seven in total. That is, in the present case example, 28 feature amounts per spectrum were calculated. Further, in the present case example, the same number of standard deviations was calculated per parameter.

On the other hand, there also exist samples and arrangement conditions that the diffraction peak could not be observed even when observing it and, in that case, the half-value width $H_k$ and the diffraction position $X_o$ to −1, the integrated intensity I to 0 and the Lorenz component ratio η to 0.5 so as to become obvious outliers, were set. All the standard deviations in that case was set to 0s. Incidentally, since pieces of data which were measured by different devices and under different measurement conditions can be handled under the same standard, it is desirable to standardize the spectral intensity to a value per integrated unit time.

A result of inspection in the above case example 1 is shown in FIG. 6. FIG. 6 is a table which indicates a relationship between the spectral feature amount and the material identifier. Specifically, it is the table which indicates results of Stratified k-Fold Cross Validation (k=6) using the Random Forest (RF) method and the Neural Network (NN) method of machine learning. In the RF method, a decision tree to 1000 kinds of data groups that ⅓ of the learning data was selected by duplicate combination is allocated, and the NN method was carried out by superposing four fully connected layers which are 50 in number of units by the stochastic gradient descent method.

Here, the identification accuracy degree is an average value of cross-validation which were performed 100 times. Specifically, since test data per verification is 19, tests amounting to 19×6×100=11400 times were conducted.

As a result, such a very high material identification accuracy degree as that which is shown in the drawing was obtained. The correlation function f of the spectral feature amount and the material identifier is, the tree structure of the RF method and the network structure of the NN method apply. A technique or an algorithm which indicates such a high material identification accuracy degree as above would become the correlation function f. Incidentally, normalization was set per spectral feature amount as preprocessing for applying the NN method. In addition, although a still higher material identification accuracy degree can be obtained by selecting the spectral feature amount to be input and it is important for operating the spectral feature amount and material identifier correlation DB 5, it does not matter even if it is not selected in carrying out each embodiment of the present invention.

Next, a display example of the feature amount error and identification accuracy degree relationship analysis unit is shown in FIG. 7. This can be displayed on the above-described display unit 8, the inspector terminal 9 or a material utilizer/applier terminal 11. In the present case example, one of models which were high in predictive performance in cross-validation by the NN method was used as the correlation function f. Specifically, a class was adopted which was the highest in probability to be output when inputting m±α that the feature amount deviation ±α was given to the spectral feature amount m per class into the correlation function f as a predicted class. In FIG. 7, the material identification accurate degree $P_\alpha$ is finally displayed to one α. Here, it is desirable for α to have a value which is equal to or less than the actual error, the display example in FIG. 7 is a case where the NN method was applied, standardization is performed per feature amount and dispersion is set to 1 and therefore it was randomly given in a range of $0 < \alpha_i \leq 1$.

Next, one example of a frequency distribution of the accuracy degree of the material identification when giving a which amounts to 10000 in a range of (a) $0 < \alpha_i \leq 0.5$, in a range of (b) $0 < \alpha_i \leq 1$ and in a range of (c) $0 < \alpha_i \leq 2$ is shown in FIG. 8. Here, the smaller the upper limit of α is taken, the more the frequency which indicates the high material identification accuracy degree is increased and the larger the upper limit of α is taken, the more the frequency which indicates the high material identification accuracy degree is decreased. The feature amount error-identification accuracy degree relationship analysis unit 6 stores the material identification accurate degree Pc, which was obtained in this way into the feature amount error-identification accuracy degree correlation DB 7. On this occasion, the feature amount error-identification accuracy degree relationship analysis unit 6 may store it in the form of a correlation function just like P(α).

In the present case example, the network structure of the NN method that we newly learned by using all pieces of data in FIG. 8 is saved as P(α). Incidentally, this network structure is the structure which is the same as the above-mentioned one and there are four binding layers that the unit number is 50 in total. Obviously, the technique or algorithm which can describe the correlation would become P(α). Since the value of the spectral feature amount itself is not included in $P_\alpha$ and P(α), it is possible for the material utilization/application business operator to disclose it to the inspection business operator.

Case Example 2

Next, the case example 2 in which an inspection process which supposed the silent change was carried out will be described. Also, in this case example, the XRD device which is the same as that in the previous case example 1 is used. If the correspondence relation between the measurement condition and the device parameter can be taken, the XRC device may be different from it and if it is a commercially available device, it will be possible to take the correspondence relation between them in most cases.

Here, spectral data which is not used when constructing the spectral feature amount-material identifier correlation DB 5 which is the above-described material DB is necessary. In order to verify the present case example, 413 pieces of spectral data that it was newly measured regarding 16 kinds of electromagnetic steel plates under 9 kinds of measurement conditions was used as the inspection data.

Naturally, presence of one piece of spectral data is sufficient for the inspection. Therefore, in the present case example, it is performed that, the following processing regarding two pieces of the spectral data I on the electromagnetic steel plates which is contained in the spectral feature amount-material identifier correlation data DB 5 and the spectral data II on the electromagnetic steel plates which is not contained in the spectral feature amount-material identifier correlation data DB 5. That is, it is approximated by a Pseudo Voigt function which is a model function which is the same as the one which was used when constructing the spectral feature amount-material identifier correlation DB 5 thereby to calculate the feature amount and the standard deviation σ. Here, a table which shows some of components of the calculated standard deviation σ is shown in FIG. 9.

Next, a content of output when inputting these standard deviations σ into $P_\alpha$ or P(α) is shown in FIG. 10. In a case where m was mapped by preprocessing of inputting into the correlation function f, it is necessary to perform mapping by which the scales of the absolute values are equalized also on σ. In the present case example, since the standardized spectral feature amount is used as m, we divided σ by the standard deviation between them. It became possible to predict the accuracy degree of the material identification by the spectral feature amount and material identifier correlation DB 5 by using the standard deviation α of the spectrum which we newly acquired in an inspection process in this way. In addition, since the standard deviation σ is used in the present case example, the accuracy degree of the material identification can be calculated also from spectral data on a material which is not contained in the spectral feature amount and material identifier correlation DB 5 and the inspector can utilize it in judgement for measurement condition selection.

Next, a table which indicates the accuracy degree of material identification in a case where the spectral feature amount m was used, and in a case where the standard deviation σ was used is shown in FIG. 11 in order to verify the precision of the present algorithm. However, prior to calculation of the accuracy degree of the material identification, the results of 56 pieces of the spectral data on the electromagnetic steel plates which are not contained in the spectral feature amount-material identifier correlation DB 5 are excluded. As shown in FIG. 11 (*a*), the most frequent value of P(α) indicated 96.2% as shown in FIG. 11(*a*). It means that most of the spectral data for verification indicates the accuracy degree of material identification of 96.2%. On the other hand, f(m) indicated the accuracy degree of material identification of 80.7%.

Here, the material identification accuracy degree of a result (94.8%) of the cross-validation by the NN method is FIG. 6 becomes higher than others. This depends on the degree of versatility of a model of the NN method which was used and it is not the essential problem. Both indicate sufficiently close values and it indicates that the algorithm of the present invention is effective.

Further, as a result which indicates effectiveness of the processing of each embodiment of the present invention, results of 12 pieces of the spectral data which were calculated that P(α) which is shown in FIG. 11(b) is less than 50% were extracted. In addition, the accuracy degree of the material identification which is predicted from f(m) became 50% and indicated a value which is lower than 80.7%. When P(α) is low, also the accuracy degree of the material identification which is predicted from f(m) becomes low. Therefore, a correlation is recognized between the material identification accuracy degrees which are predicted from P(α) and f(m). That is, it is good to collate it not with the correlation function f(m) which is high in confidentiality but with P(α) which is low in confidentiality. Since there exists no correspondence relation between m and α, information on m cannot be known from P(α) and the processing of each embodiment of the present invention is robust in the point of information leakage. Explanation about each case example ends with the above.

Implementation Examples of Each Embodiment

Figure 12:
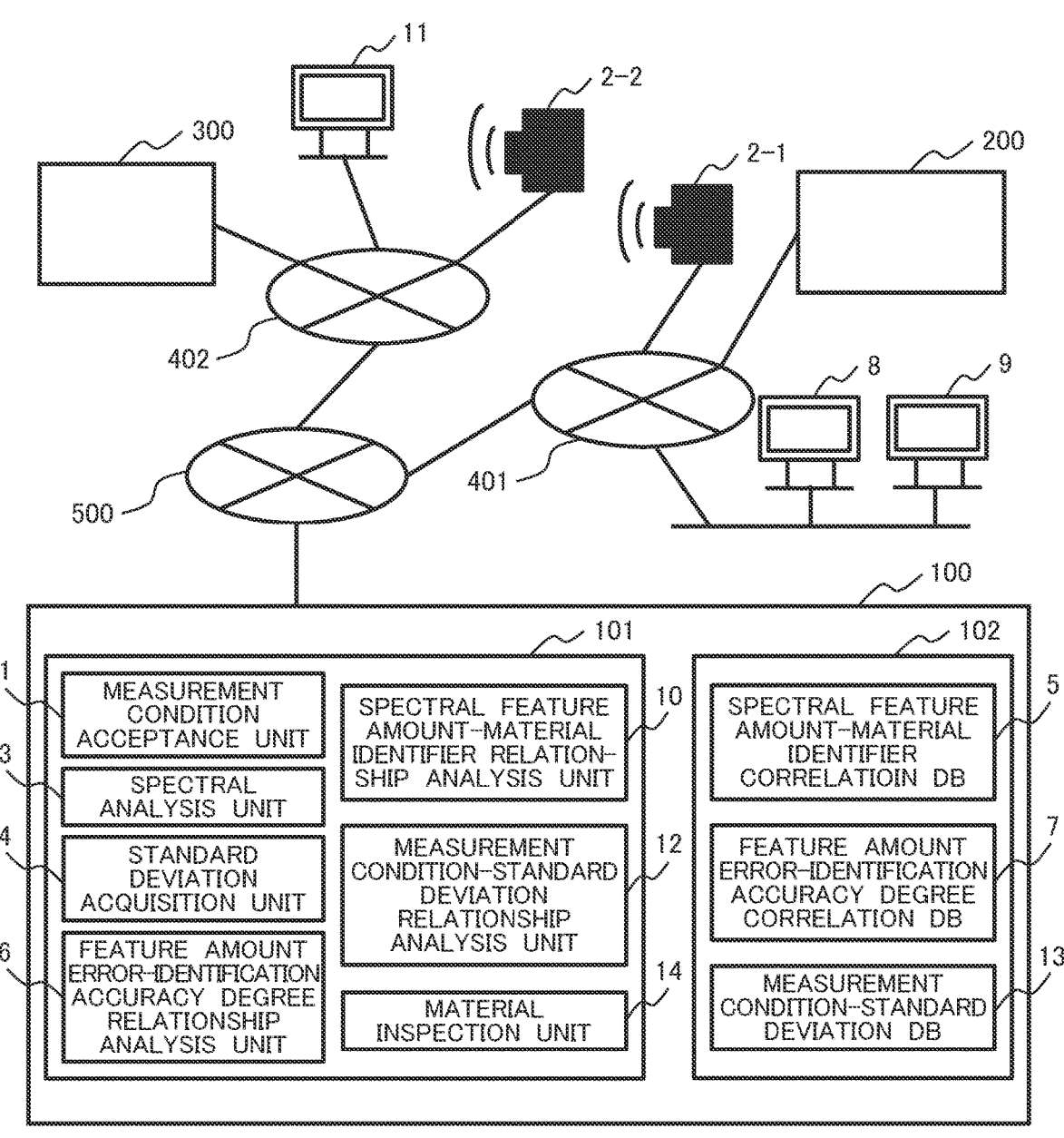
FIG. 12 is a system configuration diagram in a case where the material inspection assistance system in each embodiment was implemented by a cloud system.

Next, a configuration in a case where each embodiment has been implemented will be explained. Here, as reference signs which are utilized in FIG. 12 and later described FIG. 13, the same reference sign is assigned to a configuration which is the same as that in FIG. 1. FIG. 12 is a system configuration diagram in a case where the material inspection assistance system 1000 was implemented by a so-called cloud system. The material inspection assistance system 1000 is, the material inspection assistance device 100 is connected with an intranet 401 of the inspection business operator and an intranet 402 of the material utilization/application business operator over a network 500.

Here, an inspection business operator server 200, a terminal device which functions as the display unit 8, the inspector terminal 9 and a measurement device 2-1 are connected to the intranet 401 of the inspection business operator. In addition, a material utilization/application business operator server 300, the material utilization/application business operator terminal 11 and a measurement device 2-2 are connected to the intranet 402 of the material utilization/application business operator. Incidentally, this configuration is one example and can be partially omitted. In addition, also the number of respective devices is not limited to the number of them which is shown in the drawing.

In addition, the material inspection assistance device 100 executes main parts of the above-described processing. It has a processing device 101 and a memory device 102 for this purpose. Then, the processing device 101 has the measurement condition acceptance unit 1, the spectral analysis unit 3, the standard deviation acquisition unit 4, the feature amount error-identification accuracy degree relationship analysis unit 6, a spectral feature amount-material identifier relationship analysis unit 10, a measurement condition-standard deviation relationship analysis unit 12 and the material inspection unit 14. Incidentally, these respective configurations are ones which were described least common multiple-wise and some configurations of them can be omitted. In particular, the inspection unit 14 may be omitted or the function thereof may be put in other inspection device.

In addition, in the memory device 102, it has the spectral feature amount-material identifier correlation DB 5, the feature amount error-identification accuracy degree correlation DB 7 and the measurement condition-standard deviation DB 13. Incidentally, each of these DBs is the one which has been described least common multiple-wise and some configurations of them can be omitted.

Figure 13:
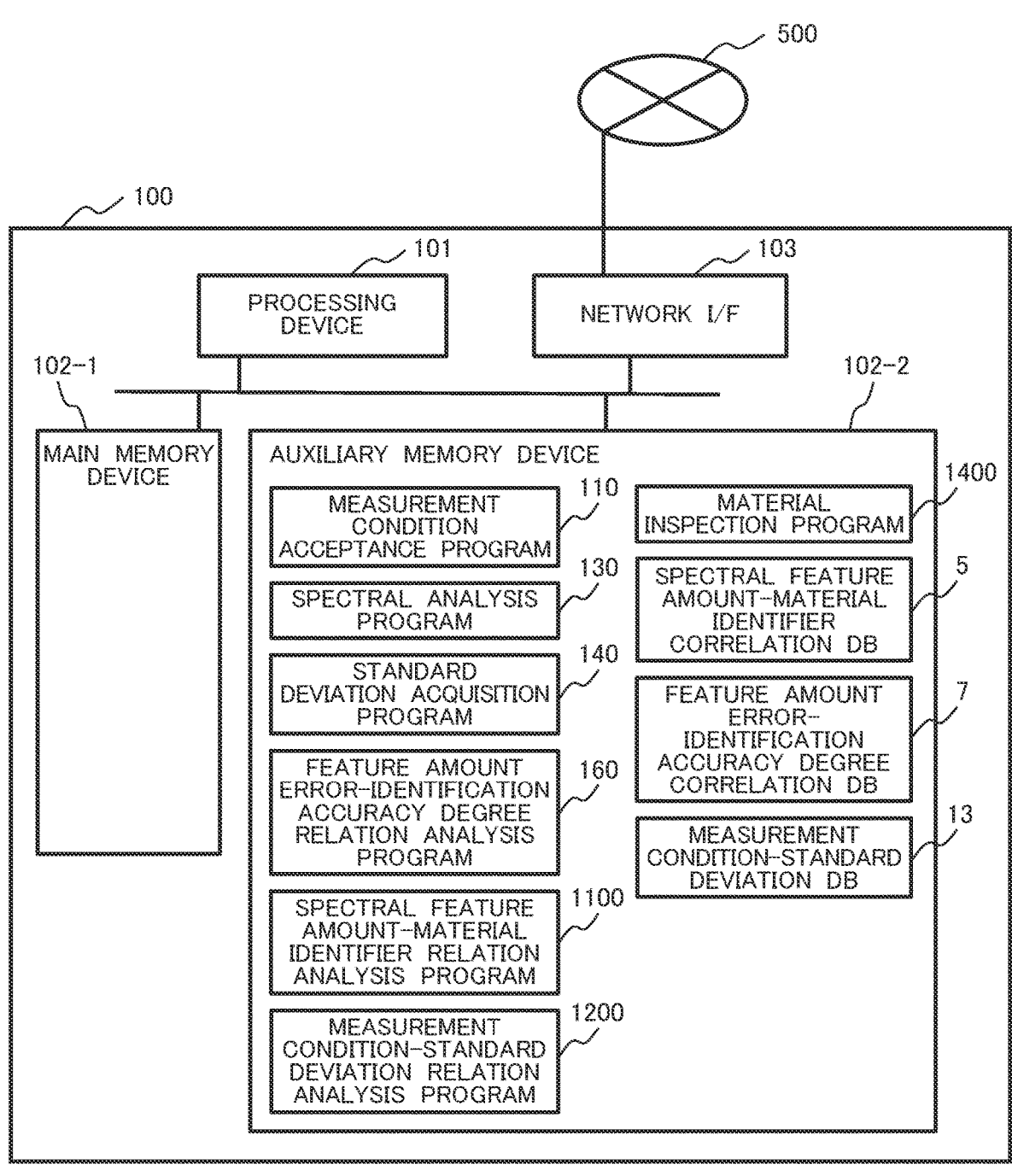
FIG. 13 is a hardware configuration diagram of the material inspection assistance device in each embodiment.

Next, in FIG. 13, it is one example of a hardware configuration diagram of the material inspection assistance device 100. The material inspection assistance device 100 is realized by a so-called computer. Therefore, the material inspection assistance device 100 has the processing device 101, a network I/F 103, a main memory device 102-1, an auxiliary memory device 102-2 and these are mutually connected via a communication path.

First, the network I/F 103 has an interface function for connecting with the network 500. In addition, the processing device 101 can be realized by a processor such as a CPU and so forth and executes arithmetic operations in accordance with each program which will be described later.

In addition, the main memory device 102-1 and the auxiliary memory device 102-2 apply to the memory device 102. Then, these can be realized by so-called memories and each program which will be described later is deployed. The auxiliary memory device 102-2 can be realized by a storage of a hard disk drive and so forth.

Then, the auxiliary memory device 102-2 installs each program and each DB therein. In the programs, a measurement condition acceptance program 110, a spectral analysis program 130, a standard deviation acquisition program 140, a feature amount error-identification accuracy degree relationship analysis program 160, a spectral feature amount-material identifier relationship analysis program 1100, a measurement condition-standard deviation relationship analysis program 1200 and a material inspection program 1400 are included. In addition, in the DBs, the spectral feature amount-material identifier correlation DB, the feature amount error-identification accuracy degree correlation DB 7 and a measurement condition-standard deviation DB 13 are included.

Here, although the processing device 101, processes thereof, arithmetic operations are executed in accordance with each program, contents thereof are the same as those of the process in each unit of each embodiment. A correspondence relation therebetween is as follows.

The measurement condition acceptance program 110: the measurement condition acceptance unit 1
The spectral feature amount-material identifier relationship analysis program 1100: the spectral analysis unit 3
The standard deviation acquisition program 140: the standard deviation acquisition unit 4
The feature amount error-identification accuracy degree relationship analysis program 160: the feature amount error-identification accuracy degree relationship analysis unit 6
The spectral feature amount-material identifier relationship analysis program 1100: the spectral feature amount-material identifier relationship analysis unit 10
The measurement condition-standard deviation relationship analysis program 1200: the measurement condition-standard deviation relationship analysis unit 12
The material inspection program 1400: the material inspection unit 14.
Incidentally, these programs may be distributed to the material inspection assistance device 100 over the network 500 and also may be memorized in the auxiliary memory device 102-2 via a memory medium which stores them. In addition, in regard to the material inspection program 1400, it may be set up in other device, in particular, an inspection device.

Incidentally, in regard to each DB, although it was set up in the memory device 102 (the auxiliary memory device 102-2), it may be set up also in other devices such as a file server and so forth. Further, although in FIG. 12 and FIG. 13, the configuration of the embodiment 2 was realized by the material inspection assistance device 100, it may be also realized by respective computer devices of the inspection business operator and the material utilization/application business operator. In this case, the functions thereof may be imparted to the above-mentioned inspection business operator server 200 and the material utilization/application business operator server 300, and the inspector terminal 9 and the material utilizer/applier terminal 11 may be realized by PCs and the functions thereof may be imparted thereto.

REFERENCE SIGNS LIST 1 measurement condition acceptance unit, 2 measurement device, 3 spectral analysis unit, 4 standard deviation acquisition unit, 5 spectral feature amount-material identifier correlation DB, 6 feature amount error-identification accuracy degree relationship analysis unit, 7 feature amount error-identification accuracy degree correlation DB, 8 display unit, 9 inspector terminal, 10 spectral feature amount-material identifier relationship analysis unit, 11 material utilizer/applier terminal, 12 measurement condition-standard deviation relationship analysis unit, 13 measurement condition-standard deviation correlation DB, 14 material inspection unit

The invention claimed is:

1. A material identification assistance device which assists identification of a material, the material identification assistance device comprising:
   a spectral analysis unit which accepts a plurality of pieces of spectral data which was acquired by a measurement device in accordance with a predetermined measurement condition to the material and calculates a spectral feature amount of the spectral data by using a model function;
   a standard deviation acquisition unit which estimates a standard deviation between the model function and a value which is actually measured by the measurement device on the basis of the spectral feature amount;
   a feature amount error-identification accuracy degree relationship analysis unit which calculates an identification accuracy degree when identifying the material by using spectral feature amount-material identifier correlation information which indicates a correspondence relation between material identifiers concerned per spectral feature amount and generates feature amount error-identification accuracy degree correlation information which indicates a correlative relation between a spectral feature amount error and the identification accuracy degree of the material by using the identification accuracy degree concerned and the standard deviation; and
   a material inspection unit which specifies an identification condition of the material on the basis of the identification accuracy degree and executes material inspection,
   wherein the identification of the material is based on at least the feature amount error-identification accuracy degree correlation information.

2. The material identification assistance device according to claim 1,
   the feature amount error-identification accuracy degree relationship analysis unit:
   (1) specifies a correlation function that a parameter value of a model function which approximated a spectrum is input and the material identifier is output from the spectral feature amount-material identifier correlation information, (2) specifies a material identifier of the material by using the correlation function,
   (3) calculates a degree of coincidence between an estimated value and a correct value of the material identifier as the accuracy degree, and
   (4) generates the feature amount error-identification accuracy degree correlation information on the basis of the accuracy degree and the standard deviation.

3. The material identification assistance device according to claim 2, wherein
   the material identification assistance device repeats the aforementioned (1) to (4) until the feature amount error-identification accuracy degree correlation information meets a correlative relationship between predetermined conditions.

4. The material identification assistance device according to claim 1, wherein
   the material identification assistance device further has a spectral feature amount-material identifier relationship analysis unit which prepares spectral feature amount-material identifier correlation information by using the spectral feature amount.

5. A material identification assisting method of assisting identification of a material using a material identification assistance device, the method comprising:
   a spectral analysis unit accepts a plurality of pieces of spectral data which was acquired by a measurement device in accordance with a predetermined measurement condition to the material and calculates a spectral feature amount of the spectral data by using a model function;
   a standard deviation acquisition unit estimates a standard deviation between the model function and a value which is actually measured by the measurement device on the basis of the spectral feature amount;
   a feature amount error-identification accuracy degree relationship analysis unit calculates an identification accuracy degree when identifying the material by using spectral feature amount-material identifier correlation information which indicates a correspondence relation between material identifiers concerned per spectral feature amount and generates feature amount error-identification accuracy degree correlation information which indicates a correlative relation between a spectral feature amount error and the identification accuracy degree of the material by using the identification accuracy degree concerned and the standard deviation; and
   specifying an identification condition of the material on the basis of the identification accuracy degree and executing material inspection, by a material inspection unit,
   wherein identification of the material is based on at least the feature amount error-identification accuracy degree correlation information.

6. The material identification assisting method according to claim 5, wherein
   the feature amount error-identification accuracy degree relationship analysis unit:
   (1) specifies a correlation function that a parameter value of a model function which approximated a spectrum is input and the material identifier is output from the spectral feature amount-material identifier correlation information,
   (2) specifies a material identifier of the material by using the correlation function, (3) calculates a degree of coincidence between an estimated value and a correct value of the material identifier as the accuracy degree, and (4) generates the feature amount error-identification accuracy degree correlation information on the basis of the accuracy degree and the standard deviation.

7. The material identification assisting method according to claim 6, wherein the material identification assisting method repeats the aforementioned (1) to (4) until the feature amount error-identification accuracy degree correlation information meets a correlative relationship between predetermined conditions.

8. The material identification assisting method according to claim 5, wherein a spectral feature amount-material identifier relationship analysis unit prepares spectral feature amount-material identifier correlation information by using the spectral feature amount.

9. A non-transitory computer readable storage medium storing a program executable by a computer, the program comprising:

a spectral analysis unit which accepts a plurality of pieces of spectral data which was acquired by a measurement device in accordance with a predetermined measurement condition to the material and calculates a spectral feature amount of the spectral data by using a model function;

a standard deviation acquisition unit which estimates a standard deviation between the model function and an actually measured value by the measurement device on the basis of the spectral feature amount; and a feature amount error-identification accuracy degree relationship analysis unit which calculates an identification accuracy degree when identifying the material by using spectral feature amount-material identifier correlation information which indicates a correspondence relation between material identifiers concerned per spectral feature amount and generates feature amount error-identification accuracy degree correlation information which indicates a correlative relation between a spectral feature amount error and the identification accuracy degree of the material by using the identification accuracy degree concerned and the standard deviation, wherein identification of the to the material is based on at least the feature amount error-identification accuracy degree correlation information, and wherein a material inspection unit which specifies an identification condition of the material on the basis of the identification accuracy degree and executes material inspection.

10. The storage medium according to claim 9, allowing the feature amount error-identification accuracy degree relationship analysis unit to execute processes of (1) specifying a correlation function that a parameter value of a model function which approximated a spectrum is input and the material identifier is output from the spectral feature amount-material identifier correlation information, (2) specifying a material identifier of the material by using the correlation function, (3) calculating a degree of coincidence between an estimated value and a correct value of the material identifier as the accuracy degree, and (4) generating the feature amount error-identification accuracy degree correlation information on the basis of the accuracy degree and the standard deviation.

11. The storage medium according to claim 10, wherein the program of making the material identification assistance device repetitively execute the aforementioned (1) to (4) until the feature amount error-identification accuracy degree correlation information meets a correlative relationship between predetermined conditions.

12. The storage medium according to claim 9, wherein the program of making the material identification assistance device further function as a spectral feature amount-material identifier relationship analysis unit which prepares spectral feature amount-material identifier correlation information by using the spectral feature amount.

* * * * *